United States Patent
Atkin et al.

(10) Patent No.: US 9,795,558 B2
(45) Date of Patent: Oct. 24, 2017

(54) DEPILATORY FORMULATIONS AND METHODS OF USING SAME

(71) Applicant: Reckitt & Colman (Overseas) Limited, Slough (GB)

(72) Inventors: Neil Atkin, Slough (GB); Samuel Dawson, Hull (GB); Anne Tindal, Hull (GB); Ana Luz Velasquez, Hull (GB)

(73) Assignee: RECKITT & COLMAN (OVERSEAS) LIMITED, Slough (GB)

( * ) Notice: Subject to any disclaimer, the term of this patent is extended or adjusted under 35 U.S.C. 154(b) by 252 days.

(21) Appl. No.: 14/418,948

(22) PCT Filed: Aug. 2, 2013

(86) PCT No.: PCT/GB2013/052074
§ 371 (c)(1),
(2) Date: Feb. 1, 2015

(87) PCT Pub. No.: WO2014/020352
PCT Pub. Date: Feb. 6, 2014

(65) Prior Publication Data
US 2015/0202140 A1    Jul. 23, 2015

(30) Foreign Application Priority Data

Aug. 2, 2012 (GB) .................................. 1213731.1
Aug. 2, 2012 (GB) .................................. 1213732.9

(51) Int. Cl.
| A61K 8/88 | (2006.01) |
| A61K 8/34 | (2006.01) |
| A61Q 9/04 | (2006.01) |
| A61K 8/81 | (2006.01) |
| A61K 8/87 | (2006.01) |
| A61K 8/891 | (2006.01) |

(52) U.S. Cl.
CPC ................ *A61K 8/88* (2013.01); *A61K 8/345* (2013.01); *A61K 8/8123* (2013.01); *A61K 8/8152* (2013.01); *A61K 8/87* (2013.01); *A61K 8/891* (2013.01); *A61Q 9/04* (2013.01); *A61K 2800/884* (2013.01)

(58) Field of Classification Search
CPC .................. A61K 8/345; A61K 8/8123; A61K 2800/884; A61K 8/87; A61K 8/88; A61K 8/891; A61K 8/8152; A61Q 9/04
See application file for complete search history.

(56) References Cited

U.S. PATENT DOCUMENTS

| 2003/0223943 A1 | 12/2003 | Uang et al. |
| 2005/0197479 A1 | 9/2005 | Pavlin |

FOREIGN PATENT DOCUMENTS

| CA | 2680215 | * | 9/2008 |
| EP | 2368541 A1 | | 9/2011 |
| EP | 2517687 A1 | | 10/2012 |
| EP | 2517688 A1 | | 10/2012 |
| EP | 2561856 A1 | | 2/2013 |
| GB | 1291377 | * | 10/1972 |
| WO | 2004096164 A1 | | 11/2004 |
| WO | 2009039158 A1 | | 3/2009 |
| WO | 2011119382 A1 | | 9/2011 |
| WO | 2011119557 A2 | | 9/2011 |
| WO | 2011119794 A2 | | 9/2011 |

OTHER PUBLICATIONS

International Preliminary Report on Patentability in Priority PCT Application No. PCT/GB2013/052074, dated Feb. 3, 2015.
International Search Report for related PCT application No. PCT/GB2013/052074, dated Dec. 18, 2013.
"Soothing Hair Removal Face Cream," GNPD; Mintel, May 201, XP002665851.
"Cicactive Repair Cream," Database GNPD [Online] Mintel; Nov. 2011, XP002717257.
"Extreme Conditions Anti-Reflection Cream SPF 50" Database GNPD [Online] Mintel; Jun. 2011, XP002717258.
Great Britain Search Report for related GB Patent Application No. GB1213723.9, dated Jun. 27, 2013.
Great Britain Search Report for related GB Patent Application No. GB1213731.1, dated Jun. 27, 2013.

* cited by examiner

*Primary Examiner* — Robert Cabral
(74) *Attorney, Agent, or Firm* — Troutman Sanders LLP; Ryan A. Schneider; Chris N. Davis

(57) ABSTRACT

The present application is directed to a formulation suitable for use as a pre-use depilatory ancillary wherein said formulation comprises a hydrophobic film-forming polymer and a suitable solvent. The application is further directed to depilatory combinations which comprise a pre-use formulation and a depilatory formulation.

39 Claims, 5 Drawing Sheets

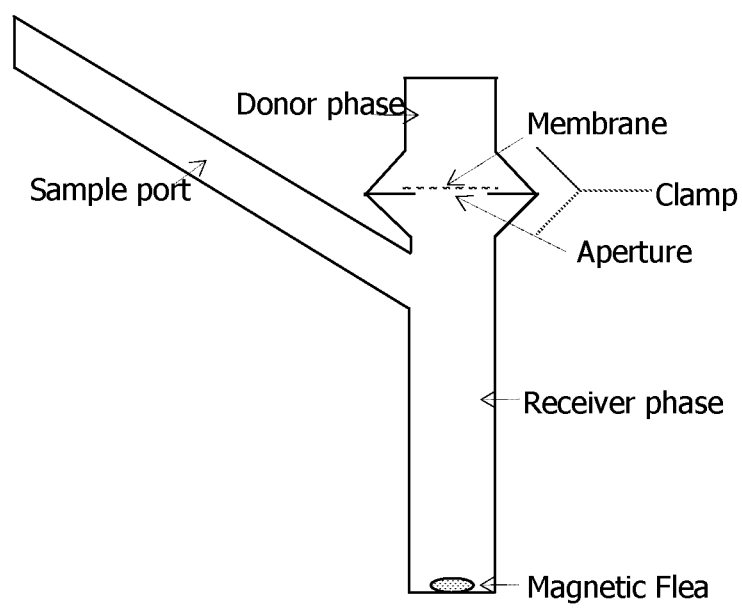
Figure 1: Schematic diagram of Franz cell apparatus

Comparative Example: Depilatory base cream
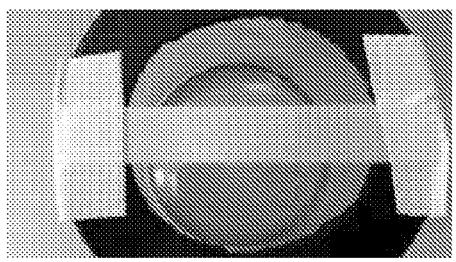
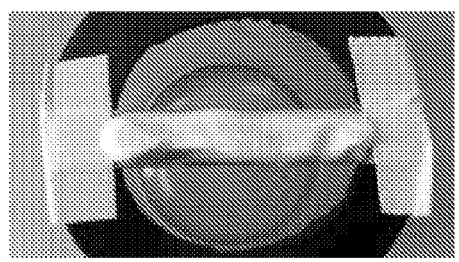
Before applicationAfter cream application
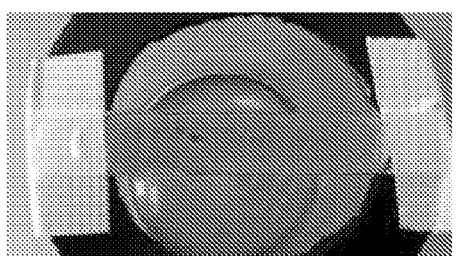
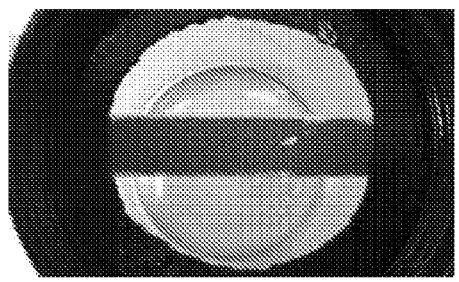
After scrapingUnderside of the pH paper
Figure 2a Example 1
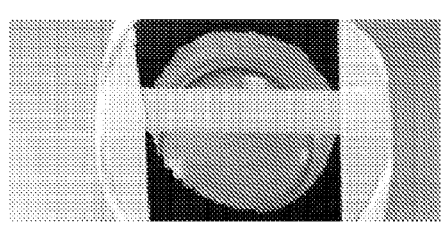
After pre-treatment application
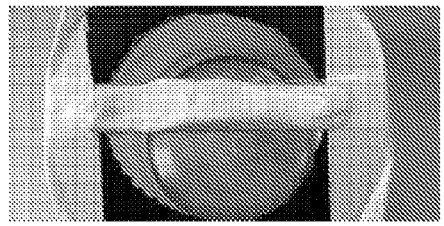
After depilatory application
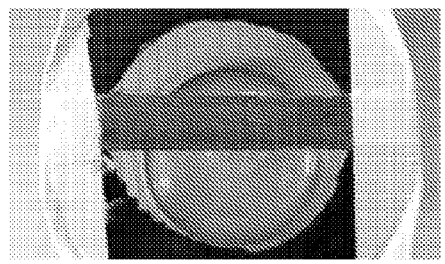
After scraping
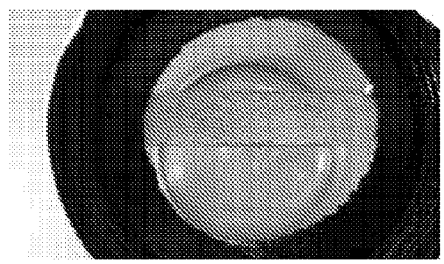
Underside of the pH paper
Figure 2b

DEPILATORY FORMULATIONS AND METHODS OF USING SAME

CROSS-REFERENCE TO RELATED APPLICATIONS

This application is a US National Stage of International Application No. PCT/GB2013/052074, filed 2 Aug. 2013, which claims the benefit of both GB 1213731.1 and 1213732.9, both filed 2 Aug. 2012, and all herein fully incorporated by reference.

The present invention is directed to a novel depilatory product. In particular, the present invention is directed a depilatory product that exhibits a lower irritancy and sensation when applied to the skin.

In general, depilatory formulations require a strong alkaline pH in order to achieve the desired action, i.e. chemical cleavage of the keratin bond in the hair. Currently, in order to achieve complete hair removal depilatory formulations must be applied to a user's skin and left for a period of up to 10 minutes prior to removal. The pH of such formulations, however, causes significant irritation to the skin of a user when applied for this length of time.

Although formulations have been developed which seek to reduce the level of irritation there remains an ongoing need for formulations that are suitable for use by individuals with especially sensitive skin.

In the art there are combination products which use a pre-treatment composition followed by a depilatory composition. However, the nature of the pre-treatment compositions is such that they prevent the depilatory formulation from properly coating the hair which means that depilation is not as efficient as it might be. WO 2004/096164 describes a combination of a lipophilic pre-treatment composition and a depilatory composition. Similar combinations are described in WO 2011/119382, WO 2011/119557 and WO 2011/119794.

BRIEF DESCRIPTION OF THE DRAWING

FIG. 1 illustrates a schematic diagram of a Franz cell apparatus.

FIGS. 2a-2b illustrate pictures of a first side of a portion of pH paper after application of a pre-treatment formulation, after application of the depilatory formulation, after removal of the depilatory formulation; and of a second side of the same portion of pH paper after removal of the depilatory formulation.

DETAILED DESCRIPTION

Figure 3:
FIG. 3 illustrates a comparison of the second side of the same portion of pH paper after removal of the depilatory formulation for Examples 2a and 2b.

According to a first aspect of the present invention there is provided a formulation suitable for use as a pre-use depilatory ancillary wherein said formulation comprises a hydrophobic film-forming polymer and a suitable solvent.

The film-forming polymer can be selected from the group consisting of polyamides, polyacrylates, acrylates, alkylacrylates, polyurethanes, fluoropolymers, silicones, or copolymers thereof. Preferably the film-forming polymer can be selected from the group consisting of polyamides, polyurethanes, fluoropolymers, silicones, or copolymers thereof. A preferred film-forming polymer is Polyamide-3.

The solvent can be selected from the group consisting of hydroxyl-containing compounds. A preferred solvent is propylene glycol.

The ratio of solvent to film-forming polymer can be selected such that the pre-use ancillary treatment is easily applied, dries quickly on the skin, and forms a protective layer. The ratio can be selected to be from between 1000:1 and 1:1. Preferably the ratio is between 100:1 and 1:1, more preferably the ratio can be between 50:1 and 1:1, and most preferably between 10:1 and 1:1. For the combination of propylene glycol and polyamide-3 a suitable ratio is between 5:1 and 2:1, preferably the ratio is 3:1.

The composition can be further provided with any suitable excipients selected from the group consisting of skin feel enhancers such as particulates (e.g. fine clay), humectants, emollients, anti-irritation compounds affecting the neurogenic and/or immunogenic pathways.

The composition can be in the form of a cream, lotion, gel or a hydrogel.

According to a second aspect of the present invention there is provided a depilatory combination which comprises at least two formulations wherein the first formulation is a pre-use depilatory ancillary that forms a barrier on the skin of an individual against a depilatory formulation and the second formulation comprises a depilatory active.

The pre-use depilatory ancillary can be a formulation as described in the first aspect of the present invention.

The combination can further include an additional formulation that acts as a post-depilatory treatment. The additional formulation can be the first formulation or any suitable formulation.

Typically the pre-use depilatory ancillary does not include a lipophilic component, or a triglyceride.

Typically, the pre-use depilatory ancillary reduces penetration of the depilatory active in the hair removal composition by less than 45%. Preferably, the pre-use depilatory ancillary reduces penetration of the depilatory active in the hair removal composition by about 20-30%.

According to a third aspect of the present invention there is provided a depilatory combination which comprises at least two formulations wherein the first formulation is a pre-treatment formulation for application to the skin of an individual and the second formulation comprises a depilatory active.

The pre-treatment formulation can be a formulation in the form of an emulsion which comprises cosmetically acceptable oil and/or wax in an aqueous base. Preferably the wax and/or oil component can be between 1 and 20% by weight, more preferably between 5 and 15% and most preferably between 8 and 12%. The emulsion can be a surfactant, polymer or stabilised particulate. The emulsion can contain skin feel enhancers, humectants, emollients, anti-irritancy ingredients including those which affect neurogenic and/or neurogenic and/or immunogenic pathways, cosmetic actives such as a ceramide as a cosmetic active.

The wax that can be used in the emulsion can comprise natural wax, synthetic wax, silicone wax, or mixtures thereof.

Suitable natural waxes include, but are not limited to, *Abies Alba* Leaf Wax, *Acacia Dealbata* Leaf Wax, *Acacia Farnesiana* Flower Wax, Beeswax, Ceresin, Cetyl Esters, *Cistus Labdaniferus* Flower Wax, *Aurantium Amara* (Bitter Orange) Flower Wax, *Aurantium Dulcis* (Orange) Peel Wax, *Copernicia Cerifera* (Carnauba) Wax, *Eclipta Prostrata* Wax, *Euphorbia Cerifera* (Candelilla) Wax, *Helichrysum Angustifolium* Wax, *Jasminum Officinale* (Jasmine) Flower Wax, *Jasminum Sambac* (Jasmine) Flower Wax, Jojoba Esters, Jojoba Wax, Lanolin Wax, *Lavandula Angustifolia* (Lavender) Flower Wax, *Lawsonia Inermis* Wax, Mink Wax, Montan Acid Wax, Montan Wax, *Myrica Cerifera* (Bayberry) Fruit Wax, *Ocimum Tenuiflorum* Wax, Olive Wax, *Oryza Sativa* (Rice) Bran Wax, Ouricury Wax, Palm Kernel Wax, *Persea Gratissima* (Avocado) Wax, *Pistacia Lentiscus* Leaf Wax, *Polianthes Tuberosa* Flower Wax, *Pyrus Malus* (Apple) Peel Wax, *Ribes Nigrum* (Black Currant) Wax, *Rosa Centifolia* Flower Wax, *Salvia Sclarea* (Clary) Wax, Shellac Wax, *Simmondsia Chinensis* (Jojoba) Butter, Soft Olive Wax, Spent Grain Wax, *Stipa Tenacissima* Wax, Sunflower Seed Wax, Vegetable Wax, *Vitis Vinifera* (Grape) Leaf Wax and mixtures thereof. Non-limiting examples of suitable synthetic waxes include Hydrogenated Japan Wax, Hydrogenated Jojoba Oil, Hydrogenated Jojoba Wax, Hydrogenated Microcrystalline Wax, Hydrogenated Rice Bran Wax, Hydrolyzed Beeswax, Microcrystalline Wax, Oxidized Beeswax, Oxidized Microcrystalline Wax, Ozokerite, Paraffin, PEG-6 Beeswax, PEG-8 Beeswax, PE G-12 Beeswax, PEG-20 Beeswax, PEG-12 Carnauba, Potassium Oxidized Microcrystalline Wax, Sulfurized Jojoba Oil, Synthetic Beeswax, Synthetic Candelilla Wax, Synthetic Carnauba, Synthetic Japan Wax, Synthetic Jojoba Oil, Synthetic Wax and mixtures thereof. Non-limiting examples of suitable silicone waxes include DC2503 Cosmetic Wax, DC580 wax, DC AMS-C30 Cosmetic Wax, C30-45 Alkyl Methicone, DC Silkywax 10, Hexamethyldisiloxane, DC ST-Wax 30, C30-45 Alkyldimethylsilyl Polypropylsilsesquioxane, DC SW-8005 resin wax, C26-28 Alkyl Dimethicone, C26-28 Alkyl Methicone, Polyphenylsilsesquioxane and mixtures thereof.

Advantageously, the wax comprises beeswax, carnauba wax, candelilla wax, jojoba wax, paraffin wax, microcrystalline wax, ozokerite, arachidyl behenate, or mixtures thereof.

The oils which can be used in the emulsion may comprise one or more oils.

The oil may be selected from natural oil, synthetic oil, silicone oil and mixtures thereof. Non-limiting examples of suitable natural oils include Acetylated Castor Oil, Acetylated Hydrogenated Castor Oil, *Actinidia Chinensis* (Kiwi), Seed Oil, *Adansonia Digitata* Oil, *Aleurites Moluccana* Seed Oil, *Anacardium Occidentale* (Cashew) Seed Oil, *Arachis Hypogaea* (Peanut) Oil, *Arctium Lappa* Seed Oil, *Argania Spinosa* Kernel Oil, *Argemone Mexicana* Oil, *Avena Sativa* (Oat) Kernel Oil, *Bertholletia Excelsa* Seed Oil, *Borago Officinalis* Seed Oil, *Brassica Campestris* (Rapeseed) Seed Oil, *Calophyllum Tacamahaca* seed oil, *Camellia Japonica* Seed Oil, *Camellia Kissi* Seed Oil, *Camellia Oleifera* Seed Oil, Canola Oil, *Carthamus Tinctorius* (Hybrid Safflower) Seed Oil, *Carthamus Tinctorius* (Safflower) Seed Oil, *Carum Carvi* (Caraway) Seed Oil, *Carya Illinoensis* (Pecan) Seed Oil, Castor Oil Benzoate, *Chenopodium Quinoa* Seed Oil, *Cibotium Barometz* Oil, *Citrullus Vulgaris* (Watermelon) Seed Oil, *Cocos Nucifera* (Coconut) Oil, Cod Liver Oil, *Coffea Arabica* (Coffee) Seed Oil, *Coix Lacryma-Jobi* (Job's Tears) Seed Oil, *Corylus Americana* (Hazel) Seed Oil, *Corylus Avellana* (Hazel) Seed Oil, *Cucumis Sativus* (Cucumber) Oil, *Cucurbita Pepo* (Pumpkin) Seed Oil, *Daucus Carota Sativa* (Carrot) Seed Oil, *Elaeis Guineensis* (Palm) Kernel Oil, *Elaeis Guineensis* (Palm) Oil, *Gossypium* (Cotton) Seed Oil, *Helianthus Annuus* (Hybrid Sunflower) Oil, *Helianthus Annuus* (Sunflower) Seed Oil, *Hippophae Rhamnoides* Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, *Isatis Tinctoria* Seed Oil, *Juglans Regia* (Walnut) Seed Oil, *Umnanthes Alba* (Meadowfoam) Seed Oil, *Unum Usitatissimum* (Linseed) Seed Oil, *Lupinus Albus* Seed Oil, *Macadamia Integrifolia* Seed Oil, *Macadamia Ternifolia* Seed Oil, Maleated Soybean Oil, *Mangifera Indica* (Mango) Seed Oil, Marmot Oil, *Melaleuca Alternifolia* (Tea Tree) Leaf Oil, *Melia Azadirachta* Seed Oil, *Melissa Officinalis* (Balm Mint) Seed Oil, Menhaden Oil, Mink Oil, *Moringa pterygosperma* Seed Oil, *Mortierella* Oil, Neatsfoot Oil, *Nelumbium Speciosum* Flower Oil, *Nigella Sativa* Seed Oil, *Oenothera Biennis* (Evening Primrose) Oil, *Olea Europaea* (Olive) Fruit Oil, *Olea Europaea* (Olive) Husk Oil, Orange Roughy Oil, *Orbignya Cohune* Seed Oil, *Orbignya Oleifera* Seed Oil, *Oryza Sativa* (Rice) Bran Oil, *Oryza Sativa* (Rice) Germ Oil, Ostrich Oil, Oxidized Corn Oil, Oxidized Hazel Seed Oil, *Papaver Orientele* (Poppy) Seed Oil, *Passiflora Edulis* Seed Oil, *Persea Gratissima* (Avocado) Oil, *Pistacia Vera* Seed Oil, Placental Lipids, *Prunus Amygdalus Amara* (Bitter Almond) Kernel Oil, *Prunus Amygdalus Dulcis* (Sweet Almond) Oil, *Prunus Armeniaca* (Apricot) Kernel Oil, *Prunus Avium* (Sweet Cherry) Seed Oil, *Prunus Cerasus* (Bitter Cherry) Seed Oil, *Prunus Persica* (Peach) Kernel Oil, *Pyrus Malus* (Apple) Oil, *Ribes Nigrum* (Black Currant) Seed Oil, *Ricinus Communis* (Castor) Seed Oil, *Rosa Canina* Fruit Oil, *Rosa Moschata* Seed Oil, Salmon Oil, *Salvia Hispanica* Seed Oil, *Santalum Album* (Sandalwood) Seed Oil, *Sesamum Indicum* (Sesame) seed oil, Shark Liver Oil, *Solanum Lycopersicum* (Tomato) Seed Oil, Soybean Lipid, Sphingolipids, *Taraktogenos Kurzii* Seed Oil, *Telphairia Pedata* Oil, Vegetable Oil, *Vitis Vinifera* (Grape) Seed Oil, *Zea Mays* (Corn) Germ Oil, *Zea Mays* (Corn) Oil and mixtures thereof.

Suitable synthetic oils include, but are not limited to, mineral oil, isopropyl pamitate, isopropyl stearate, isohexadecane, isododecane, polyglyceryl triisostearate and mixtures thereof. Suitable silicone oils include, but are not limited to, dimethicones (including partial esters of dimethicones and fatty acids derived from natural/synthetic oils), cyclomethicones, polydimethlysiloxanes (such as DC200 from Dow Corning), phenyl trimethicones, trimethyl pentaphenyl trisiloxane, dimethicone copolyols and mixtures thereof.

The combination can further include an additional formulation that acts as a post-depilatory treatment. The additional formulation can be the first formulation or any suitable formulation.

Typically, the combination is used to remove facial hair.

The depilatory formulation suitable for use in the second and third aspect of the present invention may contain a skin-feel enhancing agent selected from at least one of silicone wax, talc and polyamide resin in the depilatory cream composition.

In particular, the silicone wax, talc and/or a polyamide resin impart(s) a soft and velvety after-feel to the depilatory cream composition without affecting the composition's hair removal properties.

Talc is particularly preferred over other minerals which have previously been used in cosmetics as it confers a powdery after-feel which is desirable. In addition, it does not alter the colour of the composition. The talc may be present in an amount of 0.1 to 10 weight %, preferably 0.2 to 5 weight %, more preferably 0.5 to 3 weight %. In one embodiment, the composition includes 1 to 2 weight % talc.

The depilatory formulation may further include a humectant. Suitable humectants include polyols, such as glycerine, propylene glycol and butylene glycol. Glycerine is preferred. The humectant may be present in an amount of 0 to 10 weight %, preferably 0.5 to 5 weight %.

The composition may comprise a polyamide resin as an alternative or in addition to the mineral. The polyamide resin may be present in an amount of 0.1 to 10 weight %, preferably 0.5 to 5 weight %, more preferably 1 to 3 weight %, for example 2 weight %. The polyamide resin is preferably Nylon-12.

The composition may also comprise a silicone wax as an alternative or in addition to the mineral and/or polyamide resin. Suitable silicone waxes include $C_{30}$-$C_{45}$ alkyl methicone and a silicone wax formed from stearoxytrimethylsilane and stearyl alcohol. The silicone wax is preferably $C_{30}$-$C_{45}$ alkyl methicone.

The silicone wax may be present in an amount of 0.1 to 10 weight %, preferably 0.5 to 5 weight %, more preferably 1 to 3 weight %, for example 1 to 2 weight %.

The emollient is selected from at least one of mineral oil, silicone and emollient esters. Together with the silicone wax, mineral and/or polyamide resin (and optional humectant), the emollient plays an important role in providing the depilatory cream composition with its desired skin-feel characteristics.

The emollient may be present in an amount of 1 to 10 weight %, preferably 3 to 7 weight % of the composition.

Mineral oil may be present in an amount of 0 to 10 weight %, preferably 0.5 to 5 weight % of the composition.

Silicone oil may be present in an amount of 0 to 10 weight %, preferably 0.5 to 5 weight %, for example 1 to 4 weight % of the composition.

Emollient esters may be present in an amount of 0 to 10 weight %, preferably 0.5 to 5 weight % of the composition, for example 1 to 3 weight %.

It is possible for the emollient to consist essentially of mineral oil. For example, in one embodiment, the composition includes talc and an emollient that consists essentially of mineral oil. In this embodiment, the emollient is present in an amount of 3 to 6 weight %, preferably 5 weight %. The talc is present in an amount of 0.3 to 1 weight %, preferably 0.5 weight %. Where an emollient consisting essentially of mineral oil emollient is employed, the composition preferably includes a humectant, such as glycerine.

It is also possible for the emollient to comprise or consist essentially of silicone oil(s). Preferably, a combination of silicone oils are present. The silicone oil may include at least one of cyclopentasiloxane, dimethiconol and dimethicone. Preferably, the silicone oil comprises cyclopentasiloxane, dimethiconol and dimethicone. The silicone oil may include 0.1 to 5 weight %, preferably 1 to 2 weight % dimethicone; and/or 1 to 5 weight %, for example, 1 to 3 weight % cyclopentasiloxane and dimethiconol.

It is possible for the emollient to consist essentially of an emollient ester. However, the emollient ester is preferably used in combination with a mineral oil and/or a silicone oil.

In one embodiment, the emollient comprises at least two of mineral oil, silicone oil and emollient esters. For example, the emollient may include mineral oil and silicone oil, or mineral oil and emollient esters, or silicone oil and emollient esters. In one embodiment, the emollient includes mineral oil, silicone oil and emollient esters.

Any suitable silicone oil may be employed. Examples include cyclopentasiloxane, dimethiconol and dimethicone. The total amount of silicone oil in the composition may be 0.1 to 10 weight %, for example, 2 to 5 weight %.

Any suitable emollient ester may be employed. Suitable examples include isopropyl palmitate, isopropyl myristate, myristyl lactate, cetyl esters, isotridecyl isononanoate, $C_{12-15}$ alkyl benzoate, caprylic/capric triglyceride and pentaerythrityl tetraisostearate.

In one embodiment, the emollient comprises mineral oil. The mineral oil may be present in an amount of 3 to 6 weight %, preferably 5 weight %. In a preferred embodiment, this combination of emollients is used together with at least one of talc and polyamide resin.

The depilatory active is a compound capable of degrading keratin and may be, for example, a sulphur compound such as potassium thioglycolate, dithioetythritol, thioglycerol, thioglycol, thioxanthine, thipsalicylcic acid, N-acetyl-L-cysteine, lipic acid, $NaHSO_3$, $Li_2S$, $Na_2S$, $K_2S$, MgS, CaS, SrS, BaS, $(NH_4)_2S$, sodium dihydrolipoate 6, 8-dithiooctanoate, sodium 6,8-dithiooctanoate, salts of hydrogen sulphide for example NaSH or KSH, thioglycolic acid, thioglycerol, 2-mercaptopropionic acid, 3-mercaptropropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate and/or cysteamine. However, the composition is preferably substantially or, more preferably, is completely free from depilatory agents that destroy the thermodynamic equilibrium or the surface tension of the composition; examples of such agents include alkali metal sulphides.

Preferred depilatory compounds are thioglycolates, or their precursor thioglycolic acid. Most preferred is potassium thioglycolate, which may be produced by mixing thioglycolic acid with a neutralising source of potassium hydroxide (as noted above excess potassium hydroxide over that required to effect neutralisation cannot be used).

The depilatory active may be present in an amount of 2 to 25 weight %, preferably 5 to 20 weight %, more preferably 10 to 15 weight %. In one embodiment, the composition includes potassium thioglycolate in an amount of 2 to 25 weight %, preferably 5 to 20 weight %, more preferably 10 to 15 weight %.

The depilatory formulation of the present invention preferably includes water. Water may be present in an amount of at least 40 weight %, preferably at least 50 weight %. Suitable amounts of water range from 40 to 70 weight %, preferably 50 to 65 weight %, more preferably 55 to 60 weight %.

The depilatory formulation may optionally include one or more surfactant(s). The surfactant may be anionic, cationic or non-ionic. It is preferably non-ionic. Examples of suitable surfactants include cetearyl phosphate, cetearyl alcohol, cetearyl glucoside, cetostearyl alcohol and/or ceteareth 20. It is preferably present in an amount of from 0.5 to 15 wt % relative to the weight of the depilatory formulation, more preferably from 1 to 10 wt %.

The depilatory formulation may optionally include a source of alkalinity. This may include hydroxides, such as hydroxides of alkali and alkaline earth metals. Suitable hydroxides include sodium hydroxide, potassium hydroxide, calcium hydroxide and magnesium hydroxide. Preferably, calcium hydroxide is employed, optionally together with potassium hydroxide. The source of alkalinity (e.g. calcium hydroxide) may be present in an amount of 0.1 to 10 weight %, preferably 1 to 6 weight %, for example 2 to 5 weight % of the depilatory cream composition.

The depilatory formulation preferably has a pH of greater than 7, for example, 9 to 12.5.

Optionally, the composition includes an accelerator that will accelerate the hair removal reaction. Examples of such accelerators include urea, thiourea, dimethyl, isosorbide (DMI), ethoxydiglycol (Transcutol) or methyl propyl diol (MP diol). Preferably the accelerator is urea. The composition according to the invention preferably comprises from 5% to 15% wt, more preferably from 6 to 10 wt % of an accelerator (e.g. urea).

The depilatory formulation may comprise other optional ingredients, such as pigments and fillers, such as clays. Examples of suitable clays include sodium magnesium silicate, magnesium trisilicate and titanium dioxide. The inclusion of a clay, preferably sodium magnesium silicate, more preferably in an amount of from 0.1 to 10 wt % relative to the weight of the depilatory formulation, most preferably from 0.1 to 1 wt %, is particularly advantageous, since this provides sodium and magnesium ions for the buffer system and improves the efficiency of depilation.

The depilatory cream formulation desirably includes a chelating agent, such as sodium gluconate. The chelating agent may be present in an amount of less than 1 weight %, preferably 0.01 to 0.5 weight %, for example 0.05 to 0.1 weight %.

The depilatory cream composition may also include an additive that prevents phase separation. Suitable additives include polymers or copolymers of acrylic acid, for example, an acrylate copolymer. Such additives may be present in an amount of up to 2 weight %, preferably less than 1 weight %, more preferably less than 0.5 weight %, for example 0.1 to 0.4 weight %.

Optionally, additives such as aloe vera and Vitamin E may also be included in the composition. Such additives are employed in amounts of less than 1 weight %, for example, 0.1 to 0.5 weight % of the composition.

The depilatory formulation can be in the form of a base cream, an aerosol cream or a shower cream.

Typically the residence time is not more than 10 minutes, more preferably the residence time is between 3 and 10 minutes. The residence time can be 5 to 10 minutes.

According to a fourth aspect of the present invention there is provided a method of depilation comprising the steps of applying a pre-use depilatory ancillary as described in the first aspect of the present invention to the skin of a user wherein said ancillary forms a barrier to a depilatory formulation, applying a depilatory formulation to the skin of a user wherein the depilatory formulation comprises a depilatory active, and removing said depilatory formulation once sufficient depilation has been allowed to occur. The depilatory formulation is the same as that described in respect of the second and third aspects of the present invention.

Preferably the pre-treatment formulation is applied to the skin and gently rubbed into the surface for a period of at least 10 seconds.

Typically the pre-treatment formulation does not include a lipophilic component, or a triglyceride.

Typically, the pre-treatment formulation reduces penetration of the active in the hair removal composition by less than 45%.

Typically, the method is directed to the removal of facial hair.

According to a fifth aspect of the present invention there is provided a kit for removing hair from an area of skin comprising a pre-treatment formulation wherein said pre-treatment is as described in the first aspect of the present invention; and a depilatory formulation. The depilatory formulation is the same as that described in respect of the second and third aspects of the present invention.

Typically the pre-treatment formulation does not include a lipophilic component, or a triglyceride.

Typically, the pre-treatment formulation reduces penetration of the active in the hair removal composition by less than 45%.

Typically, the kit is used to remove facial hair.

According to a sixth aspect of the present invention there is provided a method of depilation comprising the steps of applying a pre-treatment formulation as described in respect of the second and third aspects of the present invention to the skin of a user, applying a depilatory formulation as described in respect of the third aspect of the present invention to the skin of a user wherein the depilatory formulation comprises a depilatory active, and removing said depilatory formulation once sufficient depilation has been allowed to occur.

Preferably the pre-treatment formulation is applied to the skin and gently rubbed into the surface for a period of at least 10 seconds.

Typically, the method is used to remove facial hair.

According to a seventh aspect of the present invention there is provided a kit for removing hair from an area of skin comprising a pre-treatment formulation wherein said pre-treatment formulation is as described in the third aspect of the present invention; and a depilatory formulation. The depilatory formulation is the same as that described in respect of the second and third aspects of the present invention.

Typically, the kit is used to remove facial hair.

In the context of the present application, 'pre-use ancillary' means a formulation that is applied to the skin of a user prior to application of a formulation which comprises a depilatory active. Such formulation can be referred to as a depilatory pre-treatment formulation.

Example embodiments of the present invention will now be described in more detail with reference to the accompanying Figures in which:

FIG. 1 illustrates a schematic diagram of Franz cell apparatus;

FIGS. 2a and 2b illustrate pictures of a first side of a portion of pH paper after application of a pre-treatment formulation, after application of the depilatory formulation, after removal of the depilatory formulation; and of a second side of is the same portion of pH paper after removal of the depilatory formulation; and FIG. 3 illustrates a comparison of the second side of the same portion of pH paper after removal of the depilatory formulation for Examples 2 a and 2b.

Figure 4:
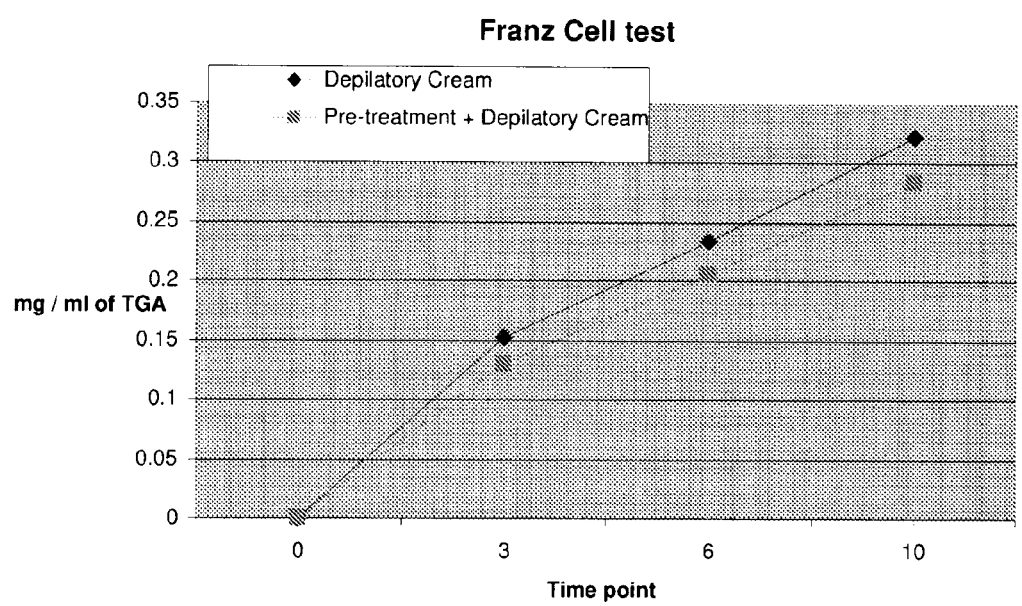
FIG. 4 depicts the results of Franz Cell testing.

FIG. 4 depicts the results of Franz Cell testing.

Examples Which Were Assessed:
    Comparative Standard Depilatory Base Cream
    Combination of pre-treatment formulation according to first aspect of the present invention and depilatory base cream An example embodiment of the pre-treatment formulation that was tested is detailed in the Table below:

| Ingredient Name | Ex. 3 % w/w |
|---|---|
| Propylene Glycol | 75 |
| Slyvaclear PA1200V (Arizona Chemicals) | 25 |
| Total | 100 |

The depilatory formulations that were tested are detailed below:

Depilatory Formulations

| Ingredient Name | Ex. 1 % w/w | Ex. 2 % w/w |
|---|---|---|
| Deionised Water | 61.74 | 66.71 |
| Cetearyl Alcohol | 4.4 | 4.4 |
| Ceteareth-20 | 1.76 | 1.76 |
| Mineral Oil | 4.8 | 4.8 |
| Glycerin | 1 | 1 |
| Talc | 2 | 2 |
| Calcium Hydroxide | 3.2 | 2.65 |
| Magnesium trisilicate | 0.5 | 0.5 |
| Sodium Gluconate | 0.1 | 0.1 |
| Na Mg Silicate | 0.2 | 0.2 |
| Urea | 8 | 4 |
| Acrylate Copolymer | 0.1 | 0.1 |
| Potassium Thioglycolate | 10 | 9.58 |
| Fragrance Citrus Glow | 0.4 | 0.4 |
| White Paste | 0.6 | 0.6 |
| Sorbitol | 1 | 1 |
| Aloe Vera | 0.1 | 0.1 |
| Vitamin E | 0.1 | 0.1 |
| Total | 100 | 100 |
| TGA | 3.00-3.30 | 3.00-3.30 |

The combinations of the present invention were assessed for diffusion of the thioglycolic acid (TGA) through a skin substitute (Franz Cell testing) and for pH barrier function.

Franz Cell—Test Method

Test Method: Determination of Thioglycolic Acid by HPLC
Reagent 1: 970 ml 0.05 M formic acid: 30 ml acetonitrile
Reagent 2: 1.90 ml formic acid: 968.1 ml deionised water: 30 ml acetonitrile Method Standard Preparation:

Using a syringe in duplicate accurately weigh approximately 100 mg of potassium thioglycolate 43% (30% TGA) into a 100 ml volumetric flask. Add 50 ml of deionised water and shake for 20 minutes. Make up to volume with deionised water and shake.

Franz Cell Setup:

4.9 ml of reagent 2 was added to the receiver cell containing a magnetic flea. The membrane was added such that no air was trapped below the membrane. The donor cell and clamp were added and the cell was allowed to stand in the stirring dry-block heater for 20 minutes until the temperature reached 37° C. An accurately weighed amount of sample (100 mg) was added to the centre of the donor cell and the counter weight (850 mg +/−10 mg) was immediately lowered on top. The counter weight ensures the product covers the total surface area of the membrane. A long tipped glass pipette was used to remove sample via the sample port directly below the aperture at the allocated collection time point.

The membrane can be pre-treated with a protective barrier wax/cream prior to adding to the receiver cell. To do this, prior to adding the membrane to the Franz Cell, lay on a clean flat surface and using a gloved finger apply the protective barrier. This should visually cover the membrane surface. Record the weight of the membrane pre and post addition of the protective layer.

HPLC Setup:

Column: Hyperclone 5 μ ODS (C18) 120 A, 100×4.6 mm or equivalent.
Phase: Reagent 1
Flow rate: 0.7 ml/min
Wave length: 240 nm 4 BW ref 6000 nm 100 BW
Run time: 10 minutes
Column temperature: 30° C.
Injection: 20 μl Calculations $$\frac{\text{Area sample}}{\text{Area standard}} \times \frac{\text{weight standard(mg)}}{100} \times 4.9 \times 0.3 = \text{mg } TGA$$

pH Barrier Function—Test Method

In this test pH indicator was used paper to determine if a depilatory base cream, or part of it, is able to penetrate below the surface of the treated area.

Method Description:

A section of pH indicator paper (FB33041—pH indicator paper reel 1 pH to 14 pH 5 m×7 mm Fisherbrand) is taped taught on the top of an open glass jar as depicted below on FIGS. 2a-2e.

The first formulation was applied lightly on one side of the pH indicator paper, and after 20 seconds the second formulation (the depilatory base cream) was applied in an even layer on top of the first formulation. The depilatory formulation was removed after a few minutes.

The colour changes on both sides of the pH indicator paper were measured to assess the penetration of the depilatory formulation through the pH indicator paper.

The depilatory base cream was applied for 3 minutes, as per pack instructions, then scraped off the pH indicator paper.

The visual assessment of the topside of the pH indicator paper, after scraping of the Depilatory cream, showed a clear change in colour in the range of pH 12 (dark blue) for all assessed samples. The colour change is comparable to the benchmark (sample 1).

The visual assessment of the underside of the pH indicator paper showed the same clear change in colour in the range of pH 12 (dark blue) for the benchmark (sample 1). For the remaining samples only slight dark blue colouring was observed on the surface of the pH indicator paper. The rest of the surface remained in its original yellow colour. It was concluded that the pre-treatment formulation provided protection of the treated surface, preventing the depilatory formulation to penetrate below it.

The combinations of the second aspect of the present invention were subjected to clinical testing for potential irritancy. The results are detailed below. A lower measurement indicates less irritancy exhibited by the combination. As can be seen there is a significant reduction in irritancy following use of the pre-use ancillary.

| Test Regimen | Chemical Depilatory test product | |
|---|---|---|
| No pre-treatment | 0.24 | 0.51 |
| Pre-use ancillary | 0.15 | 0.34 |

Examples of the Third Aspect of the Present Invention Which Were Assessed:
  Comparative standard depilatory base cream
  Combination of pre-treatment cream and depilatory base cream The example of embodiments of the pre-treatment formulation that were tested are detailed in the Table below:

Pre-Treatment Compositions

| Ingredient Name | Ex. 1 % w/w | Ex. 2 % w/w |
| --- | --- | --- |
| Deionised Water | 61.5 | 85.4 |
| Glyceryl Stearate | 3.5 | |
| Wax Emulgade 1000 (surfatant) | 5.5 | |
| Think Mineral Oil | 7 | |
| Isopropyl Palmitate | 7.5 | |
| Octyl Cocoate | 6 | |
| Octyl Stearate | 3 | |
| Bisabolol | 0.1 | |
| Zn Oxide | 0.65 | |
| Propylene Glycol | 0.35 | |
| Phenoxyethanol | 1 | |
| Tocopheryl acetate | 0.1 | |
| Na2 Phosphate | 1.2 | |
| Na phosphate | 1.1 | |
| Allantoin | 0.2 | |
| Sodium EDTA | 0.1 | |
| Ceramide | 0.5 | |
| Fragrance | 0.2 | |
| Germabenll | 0.5 | |
| Yellow Beeswax | | 5 |
| Stabylen 30 (3V Sigma) | | 0.3 |
| Cetearyl alcohol | | 3.3 |
| Glycerine | | 2 |
| Dimethicone | | 2 |
| phenoxyethanol (phenonip XB) | | 1 |
| potassium hydroxide | | 1 |
| Total | 100 | 100 |

The depilatory formulations that were tested are detailed below:

Depilatory Formulations

| Ingredient Name | Ex. 1 % w/w | Ex. 2 % w/w | Ex. 3 % w/w |
| --- | --- | --- | --- |
| Deionised Water | 61.74 | 61.74 | 66.71 |
| Cetearyl Alcohol | 4.4 | 4.4 | 4.4 |
| Ceteareth-20 | 1.76 | 1.76 | 1.76 |
| Mineral Oil | 4.8 | 4.8 | 4.8 |
| Glycerin | 1 | 1 | 1 |
| Talc | 2 | 2 | 2 |
| Calcium Hydroxide | 3.2 | 3.2 | 2.65 |
| Magnesium trisilicate | 0.5 | 0.5 | 0.5 |
| Sodium Gluconate | 0.1 | 0.1 | 0.1 |
| Na Mg Silicate | 0.2 | 0.2 | 0.2 |
| Urea | 8 | 8 | 4 |
| Acrylate Copolymer | 0.1 | 0.1 | 0.1 |
| Potassium Thioglycolate | 10 | 10 | 9.58 |
| Fragrance Scissor 081 | 0.4 | | |
| Fragrance Citrus Glow | | 0.4 | 0.4 |
| White Paste | 0.6 | 0.6 | 0.6 |
| Sorbitol | 1 | 1 | 1 |
| Aloe Vera | 0.1 | 0.1 | 0.1 |
| Vitamin E | 0.1 | 0.1 | 0.1 |
| Total | 100 | 100 | 100 |
| TGA | 3.00-3.30 | 3.00-3.30 | 2.60-3.30 |

The emulsion pre-treatment formulations are either oil or combinations of oil and wax emulsified in water. They are stabilised by either surfactants or combinations of surfactant or combinations of surfactant and polymeric emulsifier. Previously described systems were based on the use of completely anhydrous systems. By using an emulsion the product is easily rubbed into the skin and doesn't overly coat the hair as anhydrous pre-treatments can do.

The combinations of the present invention were subjected to clinical testing for potential irritancy. The results are detailed below. A lower measurement indicates less irritancy exhibited by the combination. As can be seen there is a significant reduction in irritancy following use of the pre-treatment formulation.

| Test Regimen Pre-treatment | Chemical Depilatory test product | | |
| --- | --- | --- | --- |
| Product | Example 1 | Example 2 | Example 3 |
| No pre-treatment | 0.31 | 0.24 | 0.51 |
| Example 1 | 0.09 | 0.00 | 0.00 |
| Example 2 | 0.09 | 0.09 | 0.42 |

Further modifications may be made without departing from the scope of the invention described herein.

The invention claimed is:

1. A depilatory combination comprising at least two formulations, wherein a first formulation is a pre-use depilatory ancillary formulation that forms a barrier on the skin of an individual against a depilatory formulation, and a second formulation is the depilatory formulation,
  wherein the pre-use depilatory ancillary formulation comprises:
  a hydrophobic film-forming polymer; and
  a solvent; and
  wherein the depilatory formulation comprises a depilatory active, and
  wherein the solvent is propylene glycol, the hydrophobic film-forming polymer is polyamide-3, and the ratio of the solvent to hydrophobic film-forming polymer is between 5:1 and 2:1.

2. The depilatory combination as claimed in claim 1, wherein the hydrophobic film-forming polymer of the pre-use depilatory ancillary formulation is selected from the group consisting of polyamides, polyacrylates, acrylates, alkylacrylates, polyurethanes, fluoropolymers, silicones, and copolymers thereof.

3. The depilatory combination as claimed in claim 1, wherein the solvent of the pre-use depilatory ancillary formulation is selected from the group consisting of hydroxyl-containing compounds.

4. The depilatory combination as claimed in claim 1, wherein the ratio of the solvent to the hydrophobic film-forming polymer in the pre-use depilatory ancillary formulation is selected such that the pre-use depilatory ancillary formulation is applied, dries on the skin, and forms a protective layer.

5. The depilatory combination as claimed in claim 1, wherein the pre-use depilatory ancillary formulation further comprises one or more excipients selected from the group consisting of skin feel enhancers, humectants, emollients, anti-irritation compounds affecting the neurogenic and/or immunogenic pathways and cosmetic actives.

6. The depilatory combination as claimed in claim 1, wherein the the pre-use depilatory ancillary formulation reduces penetration of the depilatory active in the depilatory formulation by less than 45%.

7. The depilatory combination as claimed in claim 1, wherein the pre-use depilatory ancillary formulation is a formulation in the form of an emulsion which comprises cosmetically acceptable wax and/or oil in an aqueous base.

8. The depilatory combination as claimed in claim 7, wherein the cosmetically acceptable wax and/or oil is between 1 and 20 weight %.

9. The depilatory combination as claimed in claim 1, wherein the pre-use depilatory ancillary formulation does not include either or both a lipophilic component and a triglyceride.

10. The depilatory combination as claimed in claim 7, wherein the emulsion is selected from the group consisting of a surfactant, polymer and particulate stabilized emulsion.

11. The depilatory combination as claimed in claim 7, wherein the emulsion contains one or more of skin feel enhancers, humectants, emollients, anti-irritancy ingredients and cosmetic actives.

12. The depilatory combination as claimed in claim 7, wherein the cosmetically acceptable wax is selected from the group consisting of natural wax, synthetic wax, silicone wax, and mixtures thereof.

13. The depilatory combination as claimed in claim 7, wherein the cosmetically acceptable oil comprises one or more oils.

14. The depilatory combination as claimed in claim 13, wherein the cosmetically acceptable oil is selected from the group consisting of mineral oil, isopropyl palmitate, isopropyl stearate, isohexadecane, isododecane, polyglyceryl tri-isostearate, silicone oil, dimethicones, cyclomethicones, polydimethlysiloxanes, phenyl trimethicones, trimethyl pentaphenyl trisiloxane, dimethicone copolyols, and mixtures thereof.

15. The depilatory combination as claimed in claim 1 further comprising a post-depilatory treatment formulation.

16. The depilatory combination as claimed in claim 1 comprising a skin-feel enhancing agent selected from the group consisting of silicone wax, talc and polyamide resin.

17. The depilatory combination as claimed in claim 1 further comprising a humectant.

18. The depilatory combination as claimed in claim 16 comprising only one skin-feel enhancing agent consisting of one of silicone wax, talc and polyamide resin.

19. The depilatory combination as claimed in claim 7, wherein the emulsion comprises a cosmetically acceptable silicone wax in an aqueous base, the silicone wax present in an amount of 0.1 to 10 weight %.

20. The depilatory combination as claimed in claim 1 further comprising an emollient selected from the group consisting of mineral oil, silicone and emollient esters.

21. The depilatory combination as claimed in claim 20, wherein the emollient is present in an amount of 1 to 10 weight %.

22. The depilatory combination as claimed in claim 1, wherein the depilatory active is a compound capable of degrading keratin and is selected from the group consisting of potassium thioglycolate, dithioetythritol, thioglycerol, thioglycol, thioxanthine, thipsalicylcic acid, N-acetyl-L-cysteine, lipic acid, $NaHSO_3$, $Li_2S$, $Na_2S$, $K_2S$, MgS, CaS, SrS, BaS, $(NH_4)_2S$, sodium dihydrolipoate 6, 8-dithiooctanoate, sodium 6,8-dithiooctanoate, NaSH, KSH, thioglycolic acid, thioglycerol, 2-mercaptopropionic acid, 3-mercaptopropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate and cysteamine.

23. The depilatory combination as claimed in claim 1 further comprising an emollient present in an amount of 1 to 10 weight % selected from the group consisting of mineral oil, silicone and emollient esters;
wherein the pre-use depilatory ancillary formulation is a formulation in the form of an emulsion comprising a cosmetically acceptable silicone wax in an aqueous base, the cosmetically acceptable silicone wax present between 0.1 to 10 weight %; and
wherein the depilatory active is present in an amount of 2 to 25 weight %.

24. The depilatory combination as claimed in claim 23 further comprising a source of alkalinity.

25. The depilatory combination as claimed in claim 24, wherein the depilatory formulation has a pH of greater than 7.

26. The depilatory combination as claimed in claim 25, wherein the depilatory formulation is in the form selected from the group consisting of a base cream, an aerosol cream and a shower cream.

27. A method of depilation using the depilatory combination as claimed in claim 1 comprising:
applying the pre-use depilatory ancillary formulation to the skin of a user;
applying the depilatory formulation to the skin of the user; and
removing the depilatory formulation once sufficient depilation has been allowed to occur.

28. The method as claimed in claim 27, wherein the pre-use depilatory ancillary formulation is applied to the skin and rubbed into the skin for a period of at least 10 seconds.

29. The method as claimed in claim 27, wherein the method is used to remove facial hair.

30. The method as claimed in claim 27, wherein the pre-use depilatory ancillary formulation reduces penetration of the depilatory active by less than 45%.

31. A kit for removing hair from an area of skin comprising the depilatory combination as claimed in claim 1.

32. The depilatory combination as claimed in claim 11, wherein the cosmetically acceptable wax and/or oil is between 5 and 15 weight %.

33. The depilatory combination as claimed in claim 11, wherein the cosmetically acceptable wax and/or oil is between 8 and 12 weight %.

34. The depilatory combination as claimed in claim 11, wherein the emulsion comprises a cosmetically acceptable silicone wax in an aqueous base, the silicone wax present in an amount of 0.5 to 5 weight %.

35. The depilatory combination as claimed in claim 11, wherein the emulsion comprises a cosmetically acceptable silicone wax in an aqueous base, the silicone wax present in an amount of 1 to 3 weight %.

36. The depilatory combination as claimed in claim 11, wherein the emulsion comprises a cosmetically acceptable silicone wax in an aqueous base, the silicone wax present in an amount of 1 to 2 weight %.

37. The depilatory combination as claimed in claim 5, wherein the emollient is present in an amount of 3 to 7 weight %.

38. The depilatory combination as claimed in claim 23, wherein the depilatory active is present in an amount of 5 to 20 weight %.

39. The depilatory combination as claimed in claim 23, wherein the depilatory active is present in an amount of 10 to 15 weight %.

* * * * *